United States Patent [19]
Caro et al.

[11] Patent Number: 5,785,659
[45] Date of Patent: Jul. 28, 1998

[54] AUTOMATICALLY ACTIVATED BLOOD PRESSURE MEASUREMENT DEVICE

[75] Inventors: Richard G. Caro; Mark H. Sher, both of San Fracisco; Bryan P. Flaherty, Half Moon Bay, all of Calif.

[73] Assignee: Vital Insite, Inc., South San Francisco, Calif.

[21] Appl. No.: 651,201

[22] Filed: May 17, 1996

Related U.S. Application Data

[63] Continuation of Ser. No. 322,261, Oct. 13, 1994, abandoned, which is a continuation-in-part of Ser. No. 228,213, Apr. 15, 1994, Pat. No. 5,590,649.

[51] Int. Cl.⁶ ............................................. A61B 5/00
[52] U.S. Cl. ........................... 600/485; 600/494; 600/500
[58] Field of Search ....................... 128/672, 677–683, 128/687–690; 600/485, 490–496, 500–503

[56] References Cited

U.S. PATENT DOCUMENTS

| | | | |
|---|---|---|---|
| 3,090,377 | 5/1963 | Salisbury et al. | 128/2.05 |
| 3,095,872 | 7/1963 | Tolles | 128/2.05 |
| 4,907,596 | 3/1990 | Schmid et al. | 128/672 |
| 5,111,817 | 5/1992 | Clark et al. | 128/633 |
| 5,237,997 | 8/1993 | Greubel et al. | 128/672 |
| 5,279,303 | 1/1994 | Kawamura et al. | 128/683 |

*Primary Examiner*—Robert L. Nasser
*Attorney, Agent, or Firm*—Flehr Hohbach Test Albritton & Herbert LLP

[57] ABSTRACT

A monitor for activating a sphygmomanometer attached to a patient includes a sensor attached to the patient to generate a sensor signal representative of a physiological parameter. This sensor can be, for example, a noninvasive sensor that generates a signal responsive to blood pressure. The monitor also has a processor coupled to the sensor and to the sphygmomanometer. The processor is configured to process the sensor signal and to send a signal to activate the sphygmomanometer when the sensor signal meets predetermined criteria.

36 Claims, 12 Drawing Sheets

AUTOMATICALLY ACTIVATED BLOOD PRESSURE MEASUREMENT DEVICE

RELATED APPLICATIONS

This patent application is a continuation of U.S. patent application Ser. No. 08/322,261 filed Oct. 13, 1994, now abandoned, which is a continuation-in-part of Caro et al., U.S. patent application Ser. No. 08/228,213 filed Apr. 15, 1994 now U.S. Pat. No. 5,590,649.

FIELD OF THE INVENTION

The present invention relates to an apparatus and method for automatically activating a blood pressure measurement device depending on a variety of sensed physiological parameters including a patient's blood pressure and other clinically important parameters.

BACKGROUND OF THE INVENTION

Blood pressure is the force within the arterial system of an individual that ensures the flow of blood and delivery of oxygen and nutrients to the tissue. Prolonged reduction or loss of pressure severely limits the amount of tissue perfusion and could therefore result in damage to or even death of the tissue. Although some tissues can tolerate hypoperfusion for long periods of time, the brain, heart and kidneys are very sensitive to a reduction in blood flow. Thus, during and after surgery, blood pressure is a frequently monitored vital sign. Blood pressure is affected, during and after surgery, by the type of surgery and physiological factors such as the body's reaction to the surgery. Moreover, blood pressure is manipulated and controlled, during and after surgery, using various medications. Often, these physiological factors and the given medications can result in a situation of rapidly changing blood pressure requiring immediate blood pressure measurement, and corrective action.

Because of changes in the patient's blood pressure, constant monitoring is important. The traditional method of measuring blood pressure is with a stethoscope, occlusive cuff and pressure manometer. However, this technique is slow, subjective in nature, requires the intervention of a skilled clinician and does not provide timely readings frequently required in critical situations.

For these reasons, two methods of measuring blood pressure have been developed: noninvasive, intermittent methods that use an automated sphygmomanometer or cuff device such as an oscillometric cuff; and invasive, continuous (beat-to-beat) measurements that use a catheter and pressure transducer.

The cuff device typically requires 15 to 45 seconds to obtain a measurement, and should allow sufficient time for venous recovery. Too frequent cuff inflations over extended periods may result in ecchymosis and/or nerve damage in the area underlying the cuff. For this reason, periodic cuff measurements should not be taken more often than approximately once every 5 minutes. This is an inordinately long amount of time to wait for an updated pressure reading when fast acting medications are administered. The invasive method has inherent disadvantages including risk of embolization, infection, bleeding and vessel wall damage.

To address the need for continuous, noninvasive blood pressure measurement, several systems were developed. One system relies on blood pressure values in a patient's finger as indicative of the patient's central blood pressure. Another system uses two cuffs, one on each arm, to determine calibration readings and continuous readings respectively. Another system transforms a time sampled blood pressure waveform into the frequency domain and determines blood pressure based on deviations of the fundamental frequency. Kaspari et al., U.S. patent application Ser. No. 08/177,448, filed Jan. 5, 1994 provides examples of these systems.

OBJECTS AND SUMMARY OF THE INVENTION

The present invention describes an apparatus and method for automatically activating a sphygmomanometer depending on a variety of parameters including a patient's blood pressure and other clinically important parameters.

An object of the present invention is to continuously monitor a sensor signal that is responsive to changes in the patient's blood pressure. A related object is to activate a cuff device when the sensor signal meets predetermined criteria.

Another object of the present invention is to induce a perturbation into a patient's blood or blood vessel and to continuously monitor a sensor signal that is responsive to changes in the patient's blood pressure. A related object is to activate a cuff device when the sensor signal meets predetermined criteria.

A monitor for activating a sphygmomanometer attached to a patient includes a sensor attached to the patient to generate a sensor signal representative of a physiological parameter. This sensor can be, for example, a noninvasive sensor that generates a signal responsive to blood pressure. The monitor also has a processor coupled to the sensor and to the sphygmomanometer. The processor is configured to process the sensor signal and to send a signal to activate the sphygmomanometer when the sensor signal meets predetermined criteria.

In operation, the monitor initially activates the sphygmomanometer to obtain a blood pressure measurement. hereafter, the sphygmomanometer is activated manually by a doctor or nurse, automatically at predetermined time intervals, or when the processor determines that the sensor signal indicates that the patient's blood pressure is sufficiently different from that previously measured.

DETAILED DESCRIPTION OF THE PREFERRED EMBODIMENTS

The embodiments described operate by sensing specific physiological parameters to automatically activate a sphygmomanometer. However, it should be understood that the present invention is directed toward a device that operates by sensing any of a plurality of physiological parameters to detect a change in the patient's blood pressure and to activate a blood pressure measuring device. In this context, the sphygmomanometer of the preferred embodiments can be substituted with any device capable of measuring blood pressure.

Those skilled in the art will appreciate that various changes and modifications can be made to the embodiments while remaining within the scope of the present invention. Moreover, currently pending patent applications incorporated herein by reference are Kaspari et al., U.S. patent application Ser. No. 08/177,448 filed Jan. 5, 1994, and Caro et al., U.S. patent application Ser. No. 08/228,213 filed Apr. 15, 1994.

Figure 1:
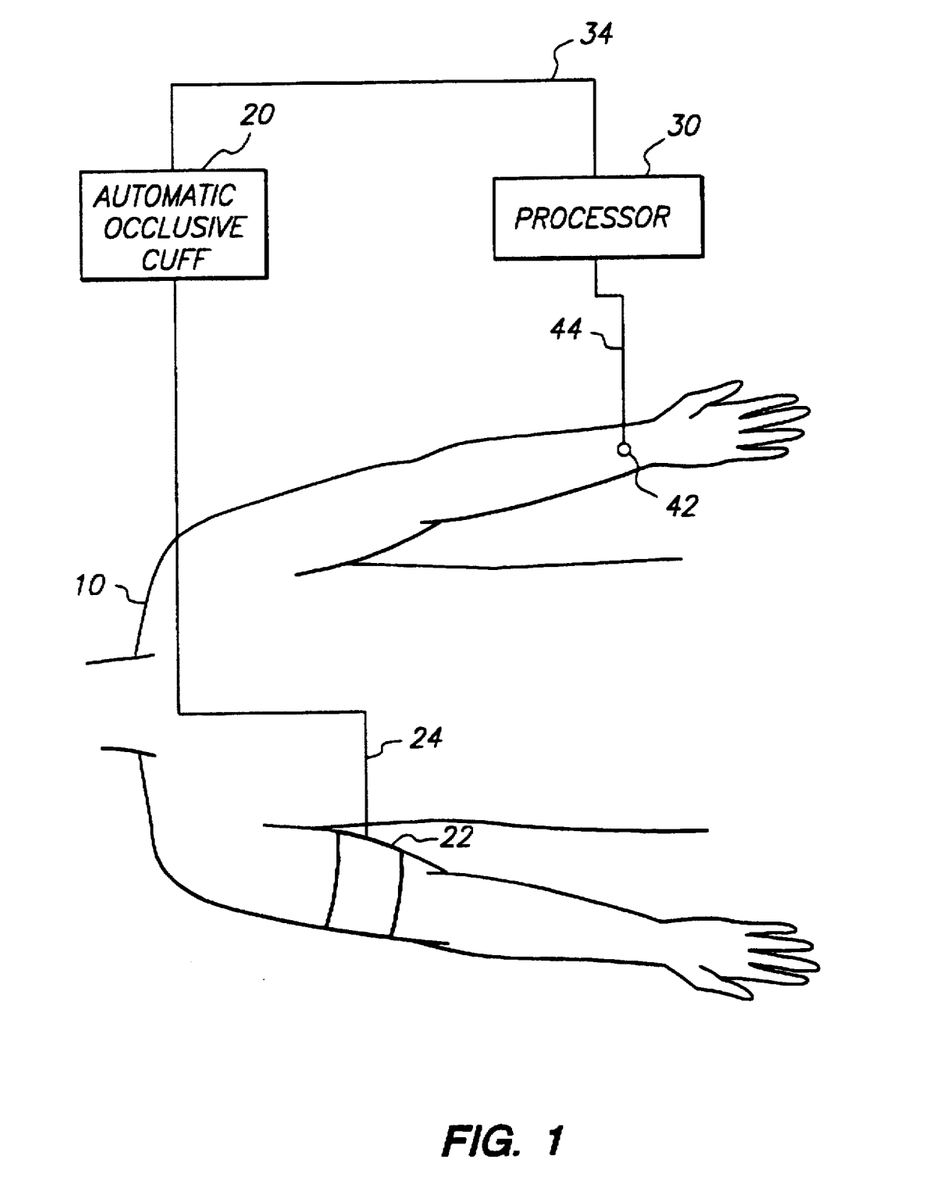
FIG. 1 depicts a first embodiment of the present invention attached to a patient.
Figure 2:
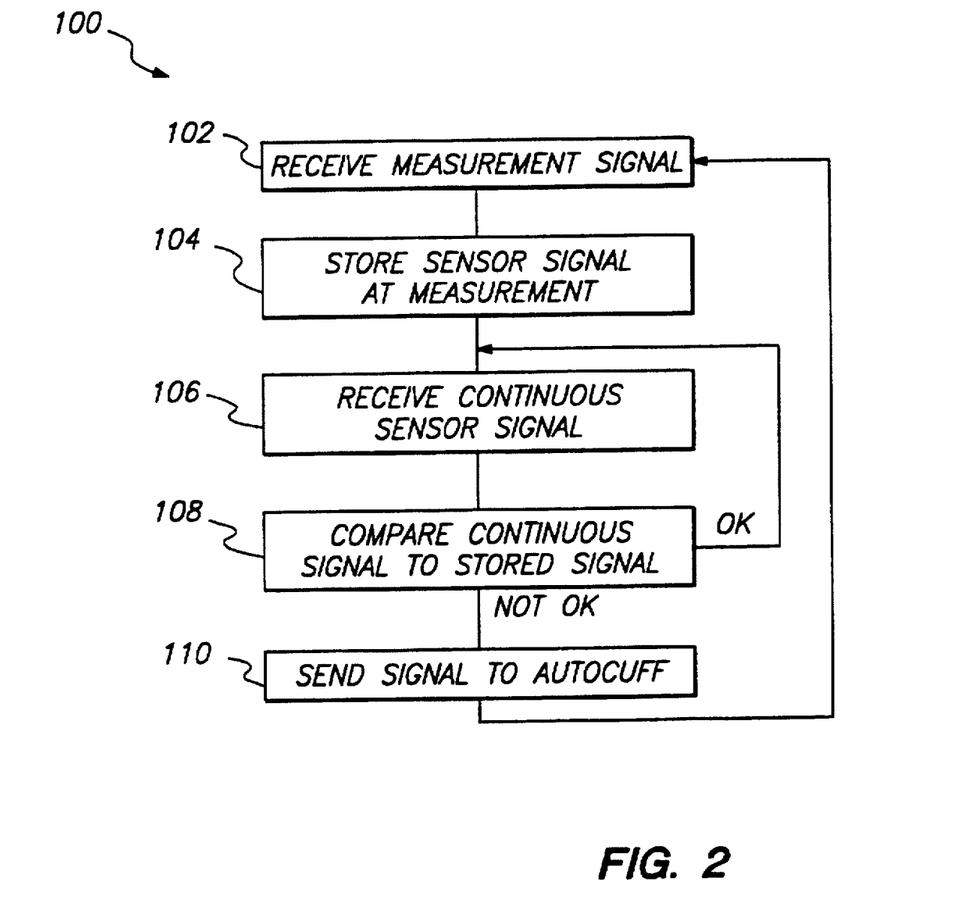
FIG. 2 depicts a flowchart showing the procedures involved in monitoring the patient for the first embodiment.

A first embodiment is explained with reference to FIGS. 1 and 2. A patient 10 is shown with an sphygmomanometer 20, 22, attached to the upper arm. The sphygmomanometer includes the control unit 20 and the cuff 22. The cuff 22 is attached to the control unit 20 via a trunk 24 that controls the inflation of the cuff 22 and receives signals from the cuff regarding the systolic and diastolic blood pressure. This type of automatic cuff is known in the art, however, an explanation of the operation is given for clarity.

In operation, the cuff 22 is attached to one of the patient's limbs, such as an arm or leg. It is even possible that the cuff be attached to the same limb as that to which any sensor is attached. The cuff is first pressurized to abate the blood flow in the limb. Then, as the pressure is slowly reduced, a transducer senses when the blood flow begins and this pressure is recorded as the systolic pressure. As the pressure is further reduced, the transducer similarly detects when full blood flow is restored and this pressure is recorded as the diastolic pressure. The signals representing pressure are delivered, via trunk 24 to control unit 20.

A processor 30 is coupled to the sphygmomanometer control unit 20 via cable 34. The processor 30 receives information regarding the patient's blood pressure from the control unit 20, and can activate the control unit 20 via the cable 34. The processor 30 is also coupled to a noninvasive sensor 42 via cable 44. The sensor 42 is a piezoelectric sensor that generates a signal related to the blood pressure at the sensor site. In FIG. 1, the sensor 42 is shown attached over the radial artery, but can be placed over any artery that is close to the skin surface. The sensor 42 generates a signal that is communicated to the processor 30 via cable 44.

A user sets a periodic measurement interval time for the sphygmomanometer, which can range from 2–60 minutes or longer. Then, the user initializes the processor 30 which begins the procedural flowchart 100 with step 102 by initializing the processor input signals. The processor 30 sends an initialization signal to the cuff control unit 20 to obtain a blood pressure measurement. The control unit 20, in turn, activates the cuff 22 and determines the blood pressure of the patient 10. Simultaneously, in step 104, the processor 30 receives the sensor signal from the sensor 42 and stores a record of the signal during measurement. Alternatively the processor stores a record of the sensor signal just before measurement or just after measurement.

During the time between measurements, in step 106, the processor 30 then receives a continuous signal from the sensor 42. The processor 30, in step 108, continuously compares the continuous sensor signal to the stored sensor signal taken during measurement. This comparison can include a comparison of periodicity, peak value, low value, waveshape, or any other factors. If, for example, waveshape is used, the processor 30 can compare the relative start time, peak time and ending time against the stored signal. If the chosen parameters conform with the testing criteria, or are within a defined bounds, then the processor continues to receive the continuous sensor signal and to compare it against the stored signal. However, if one or more of these parameters changes, the processor may determine that the patient's blood pressure has changed since the last measurement and may move to step 110 where the processor 30 sends a signal to the control unit 20 to perform a blood pressure measurement. This is the equivalent of an initial measurement as performed in step 102 and the iterative procedure begins again.

Figure 3:
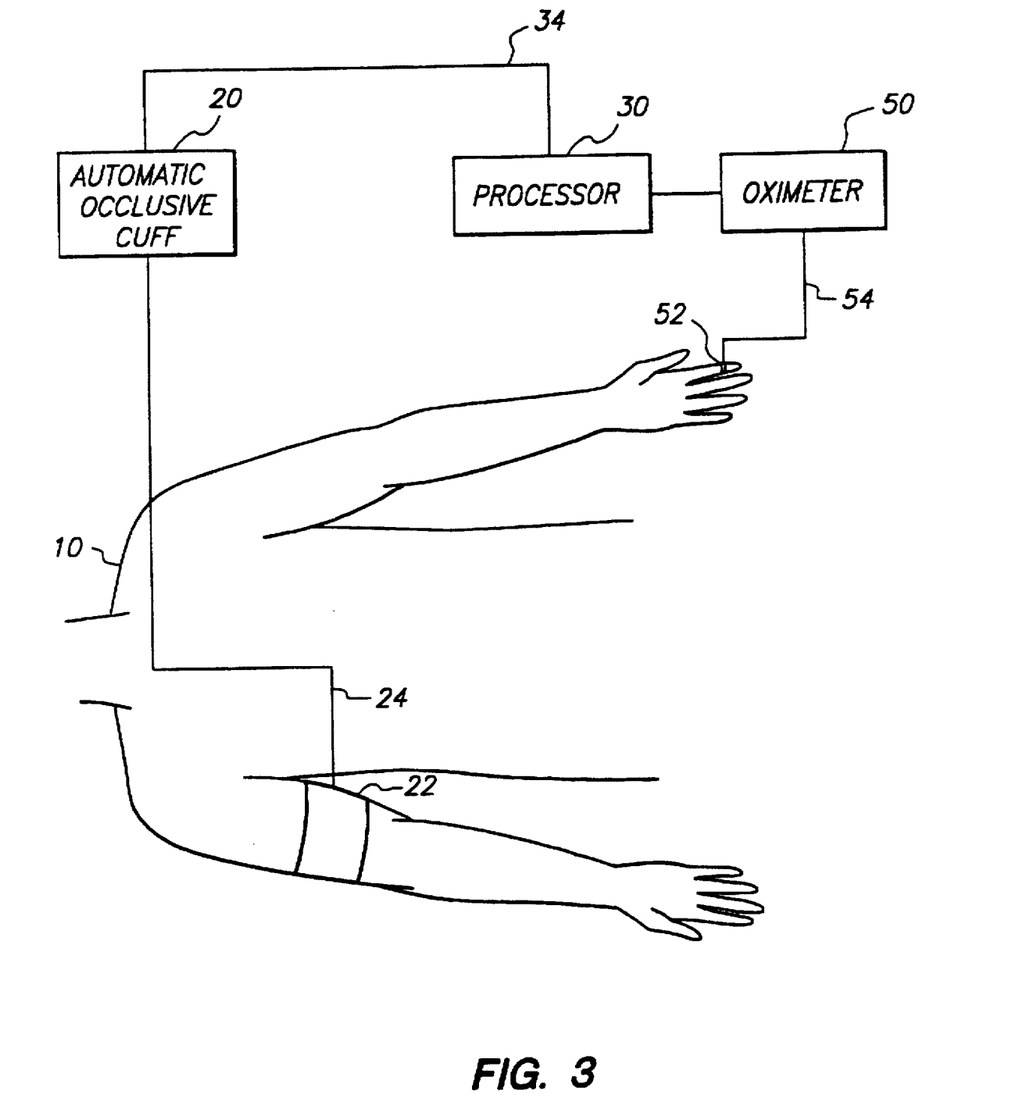
FIG. 3 depicts a second embodiment of the present invention attached to a patient.

FIG. 3 depicts a second embodiment using a photoplethysmograph. One type of photoplethysmograph, for example, is an oximeter control unit 50 coupled to an oximeter sensor 52 via cable 54. The oximeter sensor 52 performs a similar function to the noninvasive sensor 42 of the first embodiment by measuring the blood flow in a patient's extremity. The processor takes the oximeter sensor signal and performs the same procedure 100 to activate the sphygmomanometer control unit 20 as described in the first embodiment. Photoplethysmograph sensors are known in the art, and a good discussion of their functions is described in C. M. Alexander, *Principles of Pulse Oximetry: Theoretical and Practical Considerations*, Anesth Analg vol. 68 p. 368–376 (International Anesthesia Research Society 1989). In general, they shine light through an appendage, such as a finger or earlobe, and measure the attenuation of the light. The attenuation of the light has a direct relationship to the amount of oxygen in the blood, and the amount of oxygen in the blood has a direct relationship to the patient's pulse.

Figure 4:
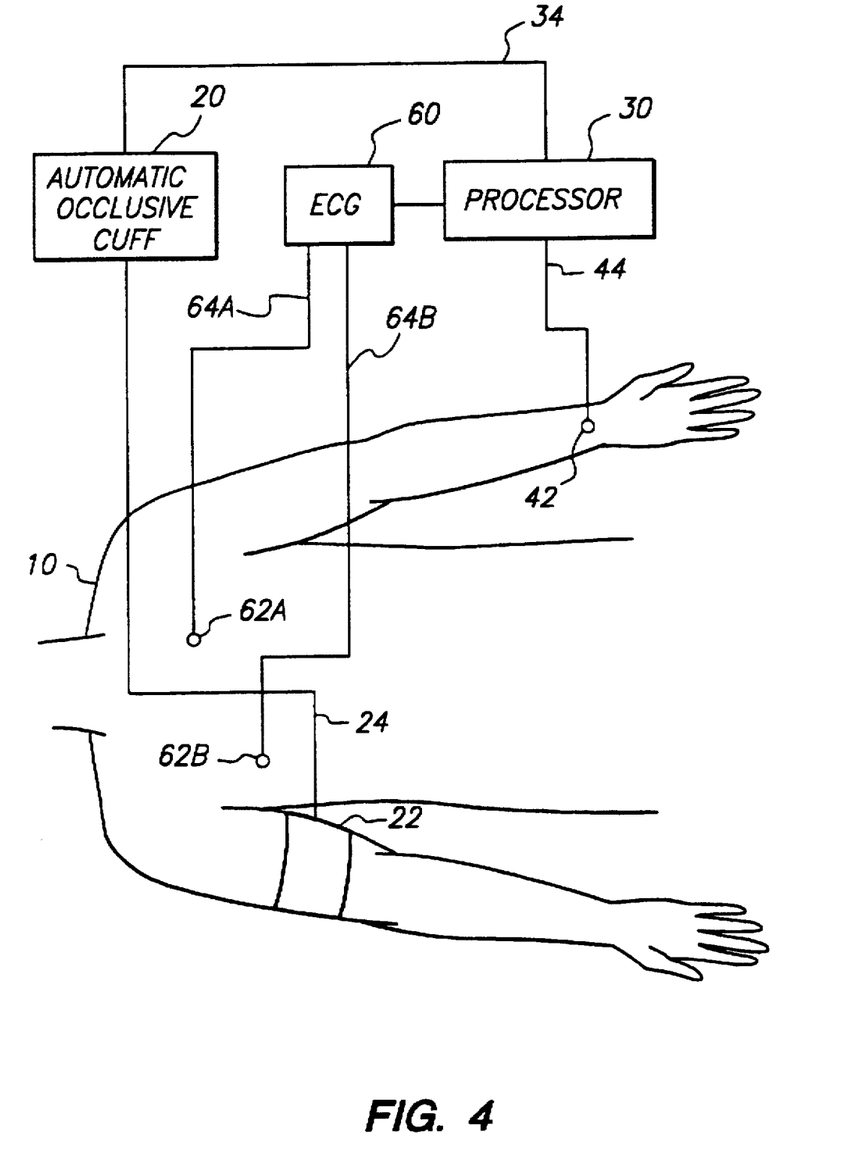
FIG. 4 depicts a third embodiment of the present invention attached to a patient.
Figure 5:
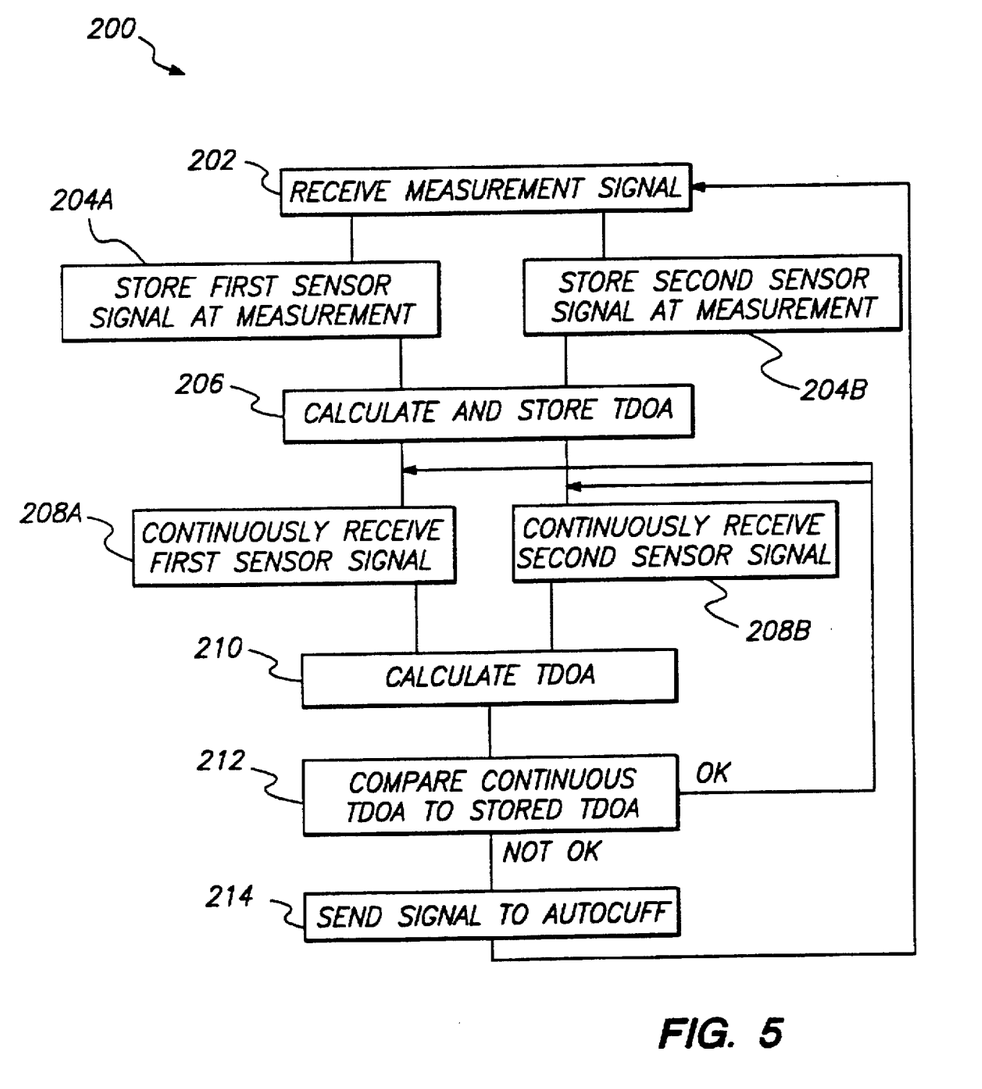
FIG. 5 depicts a flowchart showing the procedures involved in monitoring the patient for the third embodiment.

A third embodiment is described with reference to FIGS. 4 and 5. A sphygmomanometer is attached to the patient similar to the first embodiment. In this embodiment, however, the processor 30 is coupled to two sensors. The processor 30 is coupled to a noninvasive arterial sensor 42 and an electrocardiogram (ECG) unit 60, which is attached to sensor 62A and 62B via cables 64A and 64B respectively. The purpose of this configuration is to measure the time difference of arrival of the pulse at different points of the body.

A known relationship exists between pressure and velocity of a pulse. This is defined by equation 1:

$$V \propto A + BP$$

where V is velocity, A and B are constants and P is pressure. The velocity versus pressure curve is monotonic but not necessarily linear. However, the curve can be represented as piecewise linear over a range sufficient to be used in the present invention. The times of arrival at the first sensor ($T_1$) and at the second sensor ($T_2$) are subtracted to determine a time difference of arrival (TDOA). This equation is used to determine a change in blood pressure over time. Many factors are involved in the relationship between the TDOA and pressure, such as heart strength, arterial flexibility, length between the sensors and others, and they vary from patient to patient. However, since for any single patient the variables remain substantially constant for all practical purposes during the monitoring time, these factors do not need to be quantified for each patient.

Turning to the flowchart 200, the measurement step 202 is performed by activating the cuff control unit 20 and then in step 204a and 204b by receiving the ECG signal from the ECG unit 60 and receiving the noninvasive sensor signal from the noninvasive sensor 42. Then the time difference is calculated by the processor 30 in step 206, and that value is stored.

The processor continuously receives the sensor signals from the ECG unit 60 and the noninvasive sensor 42 in step 208a and 208b, and continuously determines the TDOA in step 210. A comparison of the continuous TDOA and the stored TDOA is performed in step 212. If, according to the equation 1, a change in TDOA is within predetermined bounds, then the continuous monitoring continues. An example of criteria used to determine if the TDOA is within bounds is a TDOA change of 10%, a change of 20%, or a change of 30% or more. The specific criteria can be altered and may differ depending on many factors including the patient's health, the type of surgery, the type of anesthetic and other factors.

If the processor determines that a change occurs outside a predetermined bound, then, in step 214, the processor sends a signal to the control unit 20 to initiate a new measurement. Execution of the measurement returns the processing to step 202.

Figure 6:
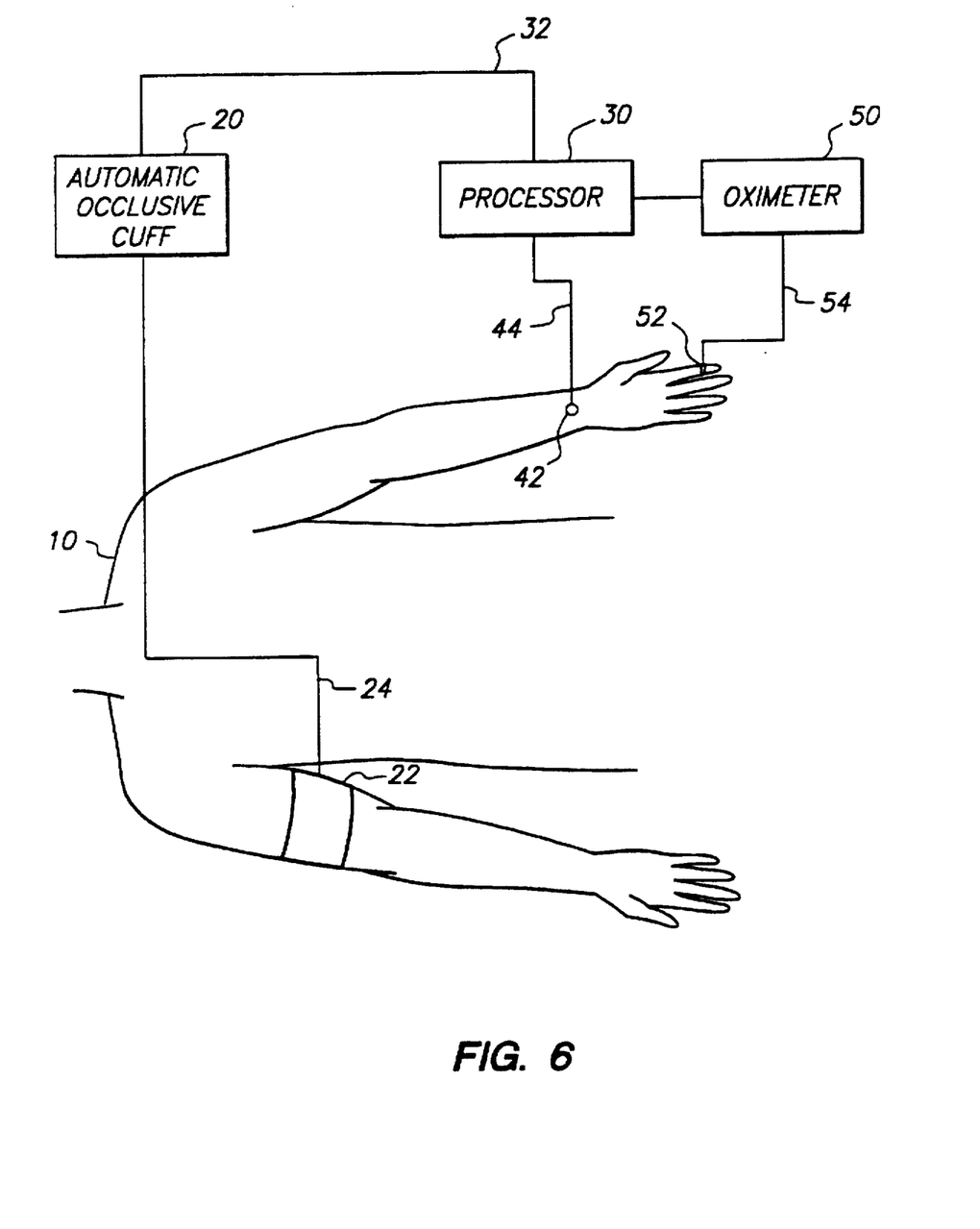
FIG. 6 depicts a fourth embodiment of the present invention attached to a patient.

FIG. 6 depicts a fourth embodiment similar to the third embodiment. The ECG unit 60 is replaced with a photoplethysmograph, such as an oximeter unit 50. The procedures performed with respect to the sensors are identical to those performed with respect to the third embodiment and are depicted in flowchart 200.

Figure 7:
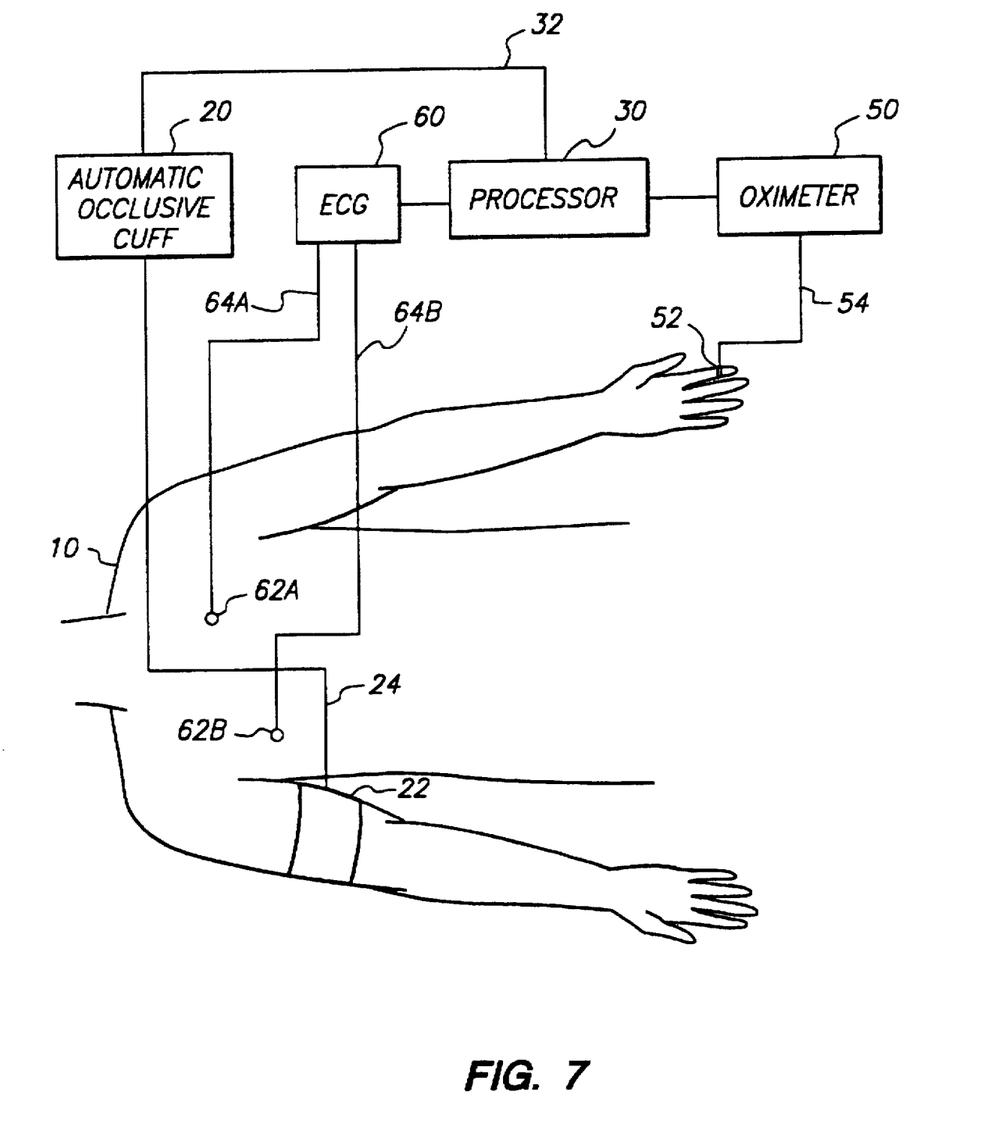
FIG. 7 depicts a fifth embodiment of the present invention attached to a patient.

FIG. 7 depicts a fifth embodiment similar to the third embodiment. The noninvasive sensor 40 is replaced with a photoplethysmograph, such as an oximeter unit 50. The procedures performed with respect to the sensors are identical to those performed with respect to the third embodiment and are depicted in flowchart 200.

Figure 8:
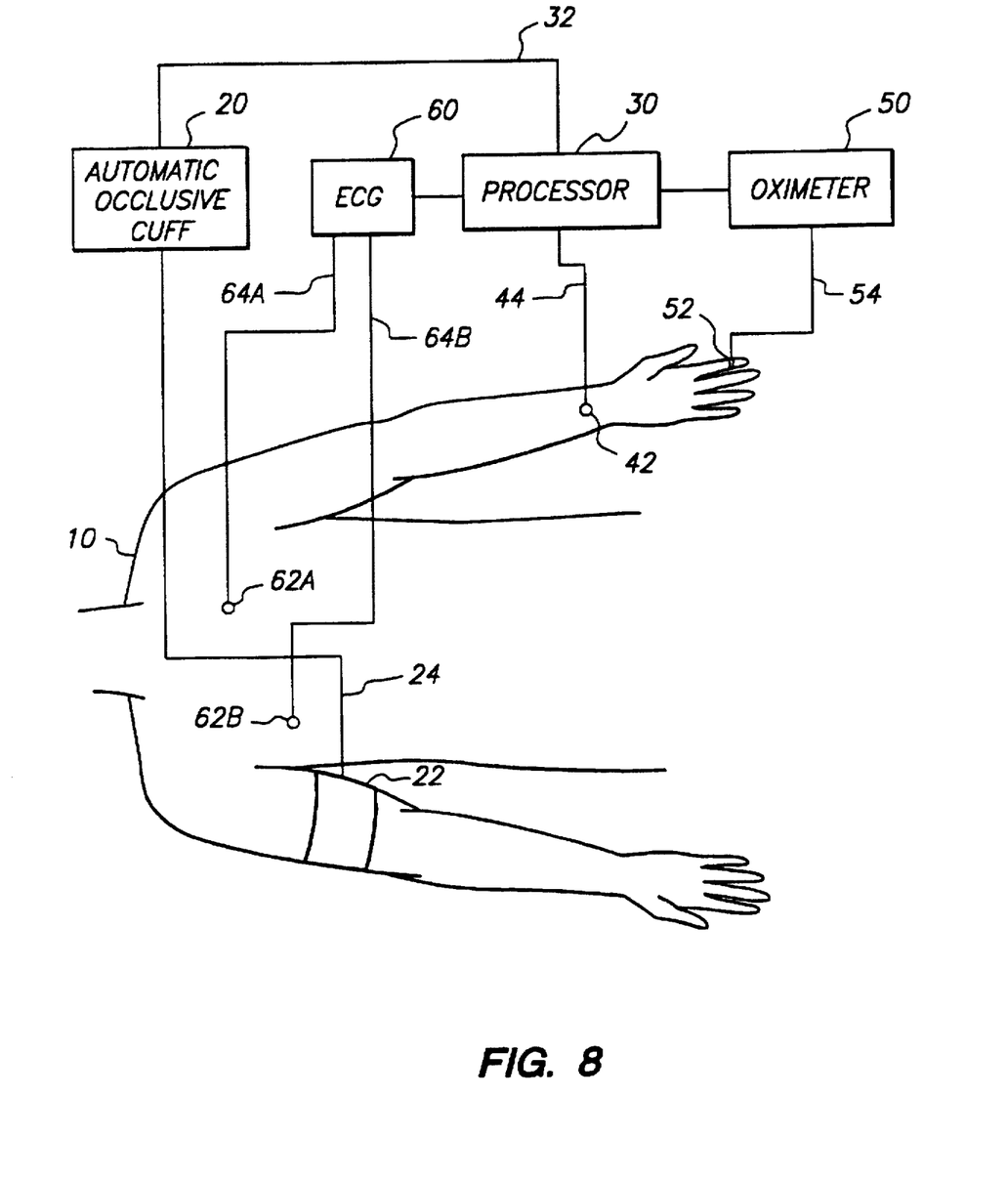
FIG. 8 depicts a sixth embodiment of the present invention attached to a patient.

FIG. 8 depicts a sixth embodiment similar to the third embodiment, but using an additional third sensor. The addition of the third sensor can be used, for example, to refine the time difference between pulse arrival at the first and second, second and third, and first and third sensors. Again, the procedures performed with respect to the sensors are identical to those performed with respect to the third embodiment and are depicted in flowchart 200.

Figure 9:
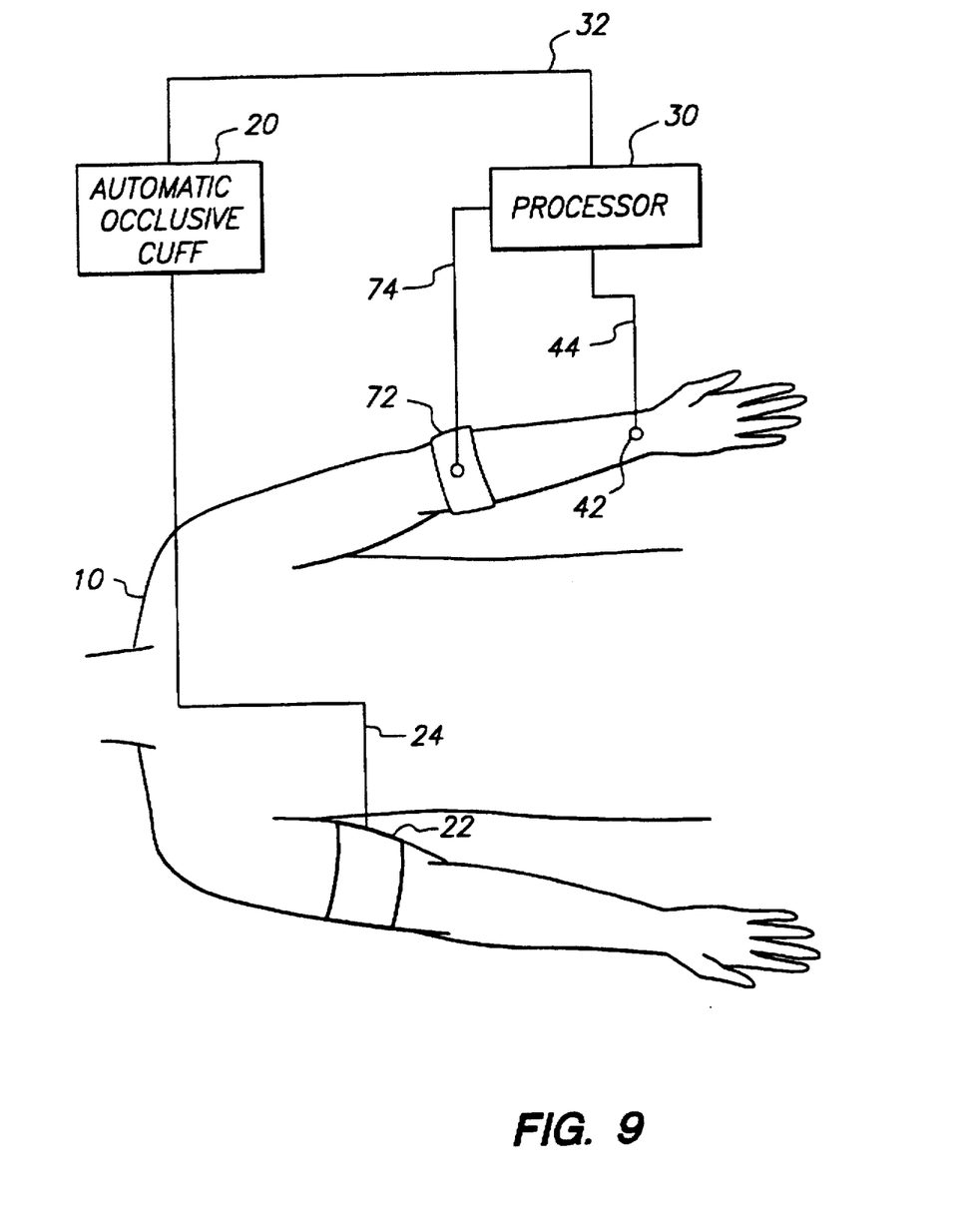
FIG. 9 depicts a seventh embodiment of the present invention attached to a patient.

FIG. 9 depicts a seventh embodiment that uses an induced perturbation to determine whether a change in blood pressure occurs. This embodiment uses the time delay between a known exciter waveform and a sensor to monitor a change in the patient's blood pressure. An exciter 72 is attached to one of the patient's limbs, such as to the forearm above the radial artery. The exciter 72 is a device for inducing a mechanical perturbation of the patient's body tissue, and can be a device such as an inflatable bag fixed in place near an accessible artery by a holddown device such as a buckle, adhesive strap or other device. Moreover, the exciter is controlled by the processor 30 via air tube 74. Alternatively, the exciter can be an electromechanical device such as a piezoelectric exciter or a solenoid exciter or other similar device, where the air tube is replaced with a wire.

The perturbation excites the tissue and blood vessel below the exciter and causes a perturbation waveform to radiate within the patient's body, at least a portion of which travels in the arterial blood. Experiments conducted to determine a range of satisfactory perturbation frequencies found that the range of 20–600 Hz works well. It is anticipated that frequencies of lesser than 20 Hz and greater than 600 Hz will also work well, and it is intended that this specification cover all frequencies insofar as the present invention is novel.

FIG. 9 further shows a noninvasive sensor 42 placed at a distance from the exciter on the patient's wrist. The noninvasive sensor is connected to the processor 30 via cable 44. As is shown, the sensor is positioned over the radial artery and it is responsive to pressure variations therein. As the pressure increases, the piezoelectric material deforms and generates a signal corresponding to the deformation.

Since a known relationship exists between blood pressure and exciter waveform velocity, a deviation in the time of transit indicates a change in blood pressure. Also, at a given frequency many other relationships are known: a relationship exists between velocity and wavelength, the greater the velocity the longer the wavelength; and a relationship exists between wavelength and phase, a change in wavelength will result in a proportional change in phase. As a result, the exciter signal is continuously measured by the sensor and a comparison is continuously made against the sensor signal stored at measurement to determine if the patient's blood pressure changes.

Figure 10:
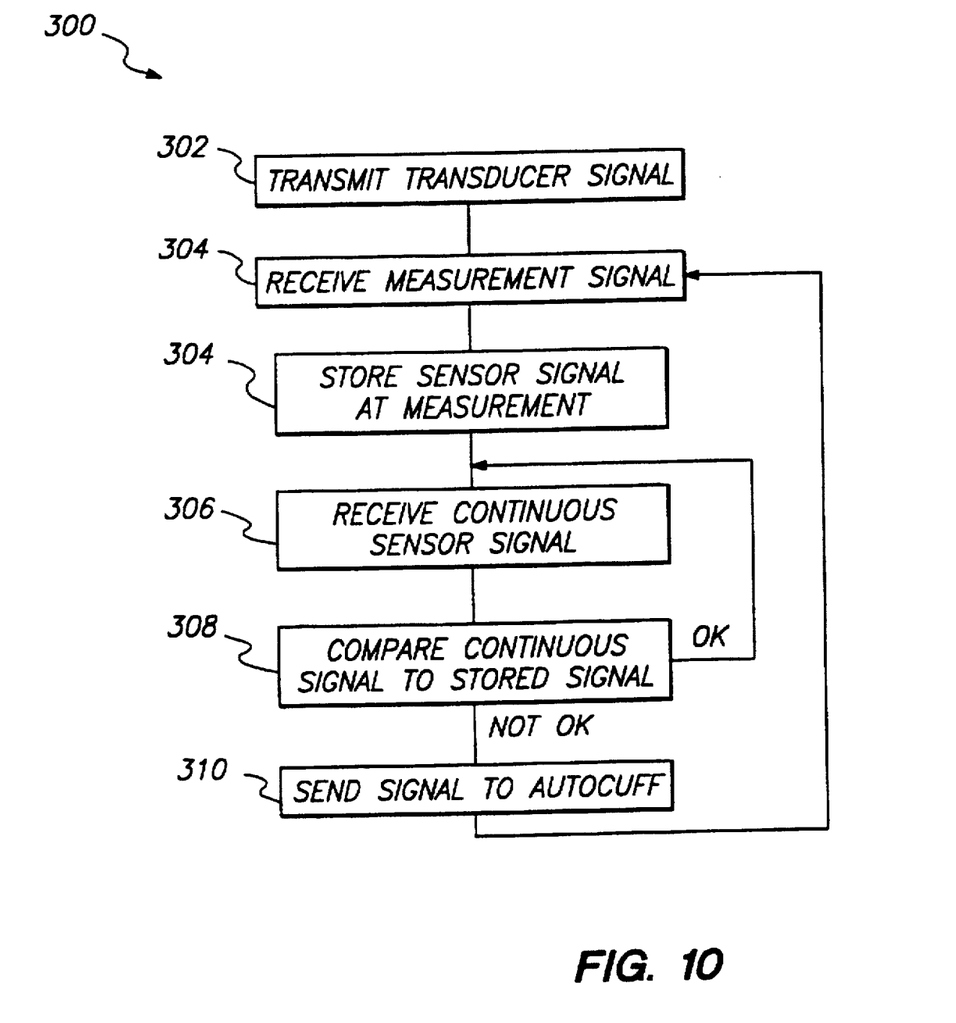
FIG. 10 depicts a flowchart showing the procedures involved in monitoring the patient for the seventh embodiment.

Referring to FIG. 10, a flow chart 300 shows the procedure used to determine whether the patient's blood pressure changes. First, the exciter signal is generated by the processor and transmitted to the exciter. A measurement step 302 activates the sphygmomanometer control unit 20 and determines the patient's blood pressure, as described above. Then the processor stores the sensor signal at measurement in step 304. In step 306, the processor continuously receives the sensor signal.

In step 308, the processor then continuously compares the continuous sensor signal to the sensor signal stored at measurement to determine if the blood pressure changes. This determination can be based on many factors including the time since the last measurement, whether the linearity of the velocity/pressure curve is outside of a reliable range, determination by medical personnel that a new measurement is desired or other factors. As an example of these factors, the embodiments provide user settable measurement time intervals of 2–60 minutes or more. For a periodic exciter waveform a known relationship exits between the phase of the continuous sensor signal and the blood pressure. This is represented by equation 2:

$$\Phi = C + DP$$

where $\Phi$ is phase, C and D are constants and P is pressure. The phase change as related to blood pressure also depends on the wavelength and frequency of the exciter wave, referring to the first equation which relates pressure and velocity. Moreover, the phase versus pressure curve is not necessarily linear, but the curve can be represented as piecewise linear over a range sufficient to be used in the present invention. Therefore, in step 308, the processor determines whether the sensor signal is valid within a predetermined phase change and within a predetermined piecewise linear region of the phase/pressure curve. If the continuous sensor signal is within bounds, the processing continues to step 306.

Step 310 is performed when step 308 determines that the prior measurement is no longer reliable as described above, such as the periodic time is expired or the patient's blood pressure changes beyond a predetermined bound. After step 310 is performed, the processing returns to step 304.

Figure 11:
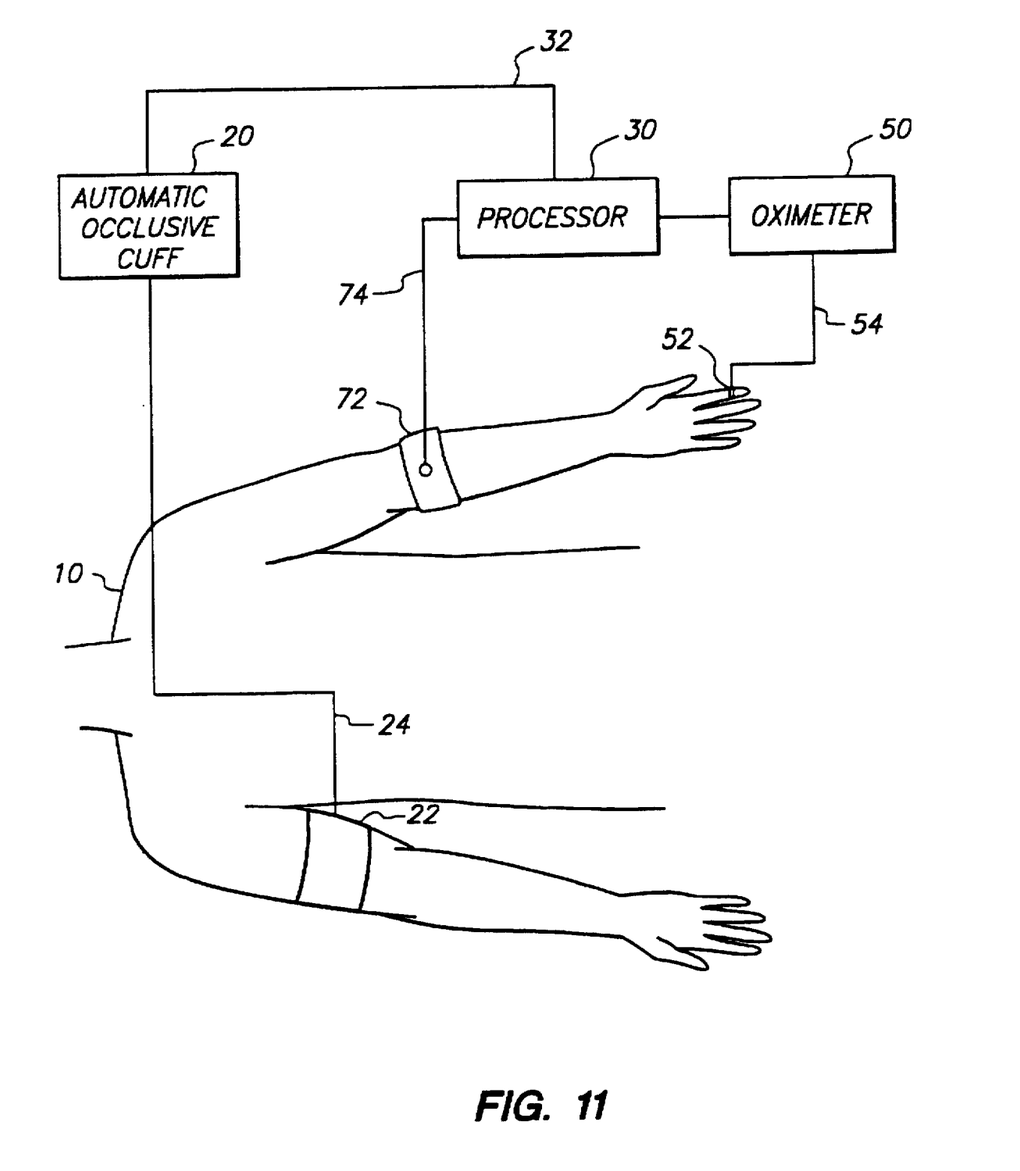
FIG. 11 depicts an eighth embodiment of the present invention attached to a patient.

FIG. 11 depicts an eighth embodiment showing the noninvasive sensor replaced by an oximeter sensor 52. This embodiment is similar to the seventh embodiment and the flowchart 300 is applicable to show the procedure for employing this embodiment.

Figure 12:
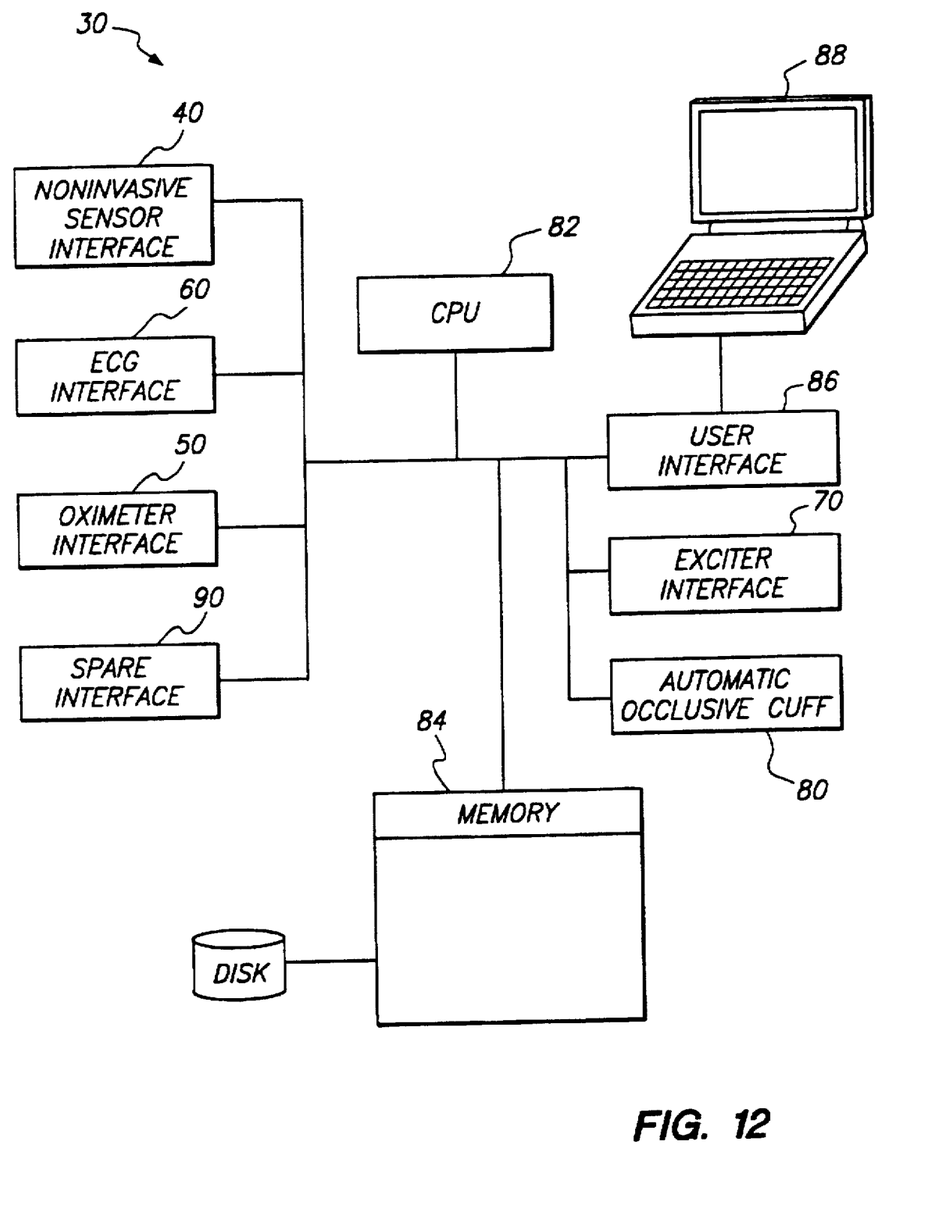
FIG. 12 depicts a processor for monitoring the patient according to the present invention.

With regard to all the embodiments, FIG. 12 depicts a processor 30 that can perform the functions of receiving the sensor signals and processing the sensor signals to determine when to activate the sphygmomanometer. The processor includes a noninvasive sensor interface 40 to receive the noninvasive sensor signal. An oximeter interface 50 is for receiving the oximeter sensor signal. An ECG interface 60 is for receiving the ECG sensor signal, which can include a plurality of inputs for a plurality of ECG sensors. An exciter interface 70 is for sending a signal to the exciter to cause a perturbation wave in the patient. A sphygmomanometer interface 80 is to receive readings from the cuff transducers and to activate the cuff when required. And, a spare interface 90 is included to receive or transmit signals to other sensors or processors.

All the device interfaces are coupled to a central processing unit (CPU) 82 and a memory 84. Moreover, a user interface 86 is included to receive input from a user and to display any required information to the user on a display 88. One skilled in the art will recognize that the processor 30 is a general purpose type computer specially configured with interfaces for required device interfaces—depending on the embodiment—and programmed to perform the procedures set forth in the present invention—again, depending on the embodiment. Alternately, processor 30 can be specially designed to perform the functions described in the invention.

VARIATIONS ON THE DISCLOSED EMBODIMENTS

Various noninvasive sensors have been developed for sensing a variety of physiological parameters. These sensor types include piezoelectric, piezoresistive, impedance plethysmograph, photoplethysmograph, various types of strain gauges, air cuffs, tonometry, conductivity, resistivity and other devices. Also, many invasive sensors can be used with the present invention, if so desired. The present invention can use any sensor that provides a waveform related to the physiological parameter of interest.

Having disclosed a preferred embodiment and the best mode, modifications and variations may be made to the disclosed embodiments without departing from the subject and spirit of the invention as defined by the following claims.

What is claimed is:

1. A monitor for indicating a change in a patient's blood pressure, comprising:

a first sensor adapted to be positioned on the patient and configured to generate a first signal representative of a physiological parameter of the patient;

a reference configured to provide a temporal reference signal;

a sphygmomanometer adapted to be attached to the patient; and a processor coupled to said first sensor, said reference and said sphygmomanometer and configured to process said first signal and said reference signal and to generate a trigger signal indicating a change in the patient's blood pressure when said first signal and said reference signal meet predetermined temporal criteria, and to activate said sphygmomanometer in response to said trigger signal.

2. The monitor of claim 1, wherein:

said reference is a second sensor adapted be positioned on the patient and configured to generate said reference signal representative of a physiological parameter of the patient.

3. The monitor of claim 2, wherein:

said predetermined criteria includes time difference of arrival criteria.

4. The monitor of claim 2, wherein:

said first sensor is a noninvasive arterial sensor configured to generate said first signal responsive to a change in arterial pressure in an artery of the patient; and said second sensor is an ECG sensor configured to generate said reference signal responsive to electrical impulses in the chest of the patient.

5. The monitor of claim 2, wherein:

said first sensor is a photoplethysmograph sensor configured to generate said first signal responsive to a change in the volume of blood in an artery of the patient; and said second sensor is an ECG sensor configured to generate said reference signal responsive to electrical impulses in the chest of the patient.

6. The monitor of claim 2, wherein:

said first sensor is a noninvasive arterial sensor configured to generate said first signal responsive to a change in arterial pressure in an artery of the patient; and said second sensor is a photoplethysmograph sensor configured to generate said reference signal responsive to a change in the volume of blood in an artery of the patient.

7. The monitor of claim 1, wherein:

said predetermined criteria includes time difference of arrival criteria.

8. The monitor of claim 1, further comprising:

an exciter adapted to be attached to the patient and configured to induce a transmitted exciter waveform into the patient;

wherein said reference signal is related to said transmitted exciter waveform.

9. The monitor of claim 8, wherein:

said predetermined criteria includes time difference of arrival criteria.

10. The monitor of claim 8, wherein:

said predetermined criteria includes phase difference criteria.

11. The monitor of claim 8, wherein:

said sensor is a noninvasive arterial sensor configured to generate said first signal responsive to a change in arterial pressure in an artery of the patient.

12. The monitor of claim 8, wherein:

said sensor is a photoplethysmograph sensor configured to generate said first signal responsive to a change in the volume of blood in an artery of the patient.

13. A processor for indicating a change in a patient's blood pressure with an apparatus having a first sensor adapted to be positioned on the patient and configured to generate a first signal representative of a physiological parameter, a reference configured to provide a temporal reference signal and a sphygmomanometer adapted to be attached to the patient, said processor comprising:

a first input configured to receive said first sensor signal;

a second input configured to receive said reference signal; and a determination routine configured to process said first signal and said reference signal and to generate a trigger signal indicating a change in the patient's blood pressure when said first signal and said reference signal meet predetermined temporal criteria; and an activation routine configured to activate said sphygmomanometer in response to said trigger signal.

14. The processor of claim 13, wherein:

said reference is a second sensor adapted be positioned on the patient and configured to generate said reference signal representative of a physiological parameter of the patient.

15. The processor of claim 14, wherein:

said predetermined criteria includes time difference of arrival criteria.

16. The processor of claim 14, wherein:

said first sensor is a noninvasive arterial sensor configured to generate said first signal responsive to a change in arterial pressure in an artery of the patient; and said second sensor is an ECG sensor configured to generate said reference signal responsive to electrical impulses in the chest of the patient.

17. The processor of claim 14, wherein:

said first sensor is a photoplethysmograph sensor configured to generate said first signal responsive to a change in the volume of blood in an artery of the patient; and said second sensor is an ECG sensor configured to generate said reference signal responsive to electrical impulses in the chest of the patient.

18. The processor of claim 14, wherein:

said first sensor is a noninvasive arterial sensor configured to generate said first signal responsive to a change in arterial pressure in an artery of the patient; and said second sensor is a photoplethysmograph sensor configured to generate said reference signal responsive to a change in the volume of blood in an artery of the patient.

19. The processor of claim 13, wherein:

said predetermined criteria includes time difference of arrival criteria.

20. The processor of claim 13, wherein said apparatus further includes an exciter adapted to be attached to the patient and configured to induce a transmitted exciter waveform into the patient, and wherein:

said reference signal is related to said transmitted exciter waveform.

21. The processor of claim 20, wherein:

said predetermined criteria includes time difference of arrival criteria.

22. The processor of claim 20, wherein:

said predetermined criteria includes phase difference criteria.

23. The processor of claim 20, wherein:

said first sensor is a noninvasive arterial sensor configured to generate said first signal responsive to a change in arterial pressure in an artery of the patient.

24. The processor of claim 20, wherein:

said first sensor is a photoplethysmograph sensor configured to generate said first signal responsive to a change in the volume of blood in an artery of the patient.

25. A method of generating a signal to indicate a change in a patient's blood pressure, said method comprising the steps of:

sensing a physiological parameter of the patient via a first sensor and receiving a first signal representative of said physiological parameter;

receiving a temporal reference signal;

processing said first signal and said reference signal and generating a trigger signal indicating a change in the patient's blood pressure when said first signal and said reference signal meet predetermined temporal criteria; and activating a sphygmomanometer in response to said trigger signal.

26. The method of claim 25, wherein:

said step of receiving a reference signal is performed by sensing a physiological parameter of the patient via a second sensor and receiving said reference signal representative of said physiological parameter.

27. The method of claim 26, wherein:

said predetermined criteria includes time difference of arrival criteria.

28. The method of claim 26, wherein:

said step of receiving a first signal is performed by a noninvasive arterial sensor configured to generate said first signal responsive to a change in arterial pressure in an artery of the patient; and said step of receiving a reference signal is performed by an ECG sensor configured to generate said reference signal responsive to electrical impulses in the chest of the patient.

29. The method of claim 26, wherein:

said step of receiving a first signal is performed by a photoplethysmograph sensor configured to generate said first signal responsive to a change in the volume of blood in an artery of the patient; and said step of receiving a reference signal is performed by an ECG sensor configured to generate said reference signal responsive to electrical impulses in the chest of the patient.

30. The method of claim 26, wherein:

said step of receiving a first signal is performed by a noninvasive arterial sensor configured to generate said first signal responsive to a change in arterial pressure in an artery of the patient; and said step of receiving a reference signal is performed by a photoplethysmograph sensor configured to generate said reference signal responsive to a change in the volume of blood in an artery of the patient.

31. The method of claim 25, wherein:

said predetermined criteria includes time difference of arrival criteria.

32. The method of claim 25, further comprising the step of:

inducing a transmitted exciter waveform into the patient; and wherein said step of receiving a reference signal is performed by receiving a reference signal related to said transmitted exciter waveform.

33. The method of claim 32, wherein:

said predetermined criteria includes time difference of arrival criteria.

34. The method of claim 32, wherein:

said predetermined criteria includes phase difference criteria.

35. The method of claim 32, wherein:

said step of receiving a first signal is performed by a noninvasive arterial sensor configured to generate said first signal responsive to a change in arterial pressure in an artery of the patient.

36. The method of claim 32, wherein:

said step of receiving a first signal is performed by a photoplethysmograph sensor configured to generate said first signal responsive to a change in the volume of blood in an artery of the patient.

* * * * *